United States Patent [19]

Lowen

[11] Patent Number: 5,101,042
[45] Date of Patent: Mar. 31, 1992

[54] PROCESS FOR THE PREPARATION OF INSECTICIDAL, NEMATICIDAL AND ACARICIDAL 2-HALO-3-SUBSTITUTED-5-ARYLPYRROLE COMPOUNDS

[75] Inventor: Gregory T. Lowen, Durham, N.C.

[73] Assignee: American Cyanamid Company, Stamford, Conn.

[21] Appl. No.: 625,738

[22] Filed: Dec. 11, 1990

[51] Int. Cl.⁵ .................. C07D 207/02; C07D 207/30
[52] U.S. Cl. ...................... 548/531; 548/561
[58] Field of Search .................. 548/531, 561

[56] References Cited

U.S. PATENT DOCUMENTS 4,709,053 11/1987 Martin ................................. 548/561
4,912,229 3/1990 Wollweber ......................... 548/561
5,041,556 8/1991 Lowen ................................. 548/561

OTHER PUBLICATIONS

CA: 90: 137608(9) Simon et al., pp. 137603–494 (1978).
CA 111: 194576w Brown et al. (1987).
CA 111: 111037x Herman et al., p. 271 (1987).
CA 113: 115076y Froyd et al. (1988).

Primary Examiner—Mary C. Lee
Assistant Examiner—Joseph K. McKane
Attorney, Agent, or Firm—Alice C. Brennan

[57] ABSTRACT

There is provided a process for the preparation of 2-halo-3-substituted-5-arylpyrrole compounds which are useful as insecticidal, nematicidal and acaricidal agents.

4 Claims, No Drawings

PROCESS FOR THE PREPARATION OF INSECTICIDAL, NEMATICIDAL AND ACARICIDAL 2-HALO-3-SUBSTITUTED-5-ARYLPYRROLE COMPOUNDS

BACKGROUND OF THE INVENTION

Arylpyrrole compounds useful as insecticides, nematicides and acaricides and the preparation thereof from acrylonitrile and substituted N-(trimethylsilyl)methyl-5-methylbenzenethioimidate compounds are described in copending patent application Ser. No. 392,495 filed on Aug. 11, 1989.

V. S. Karavan et al., Journal of Organic Chemistry (USSR), 5, pages 2161–2164 (1969) describe the preparation of 2-amino-3-cyano-5-arylfurans from the base catalysis of (substituted phenacyl)malononitrile compounds. However, no ring-closure to a pyrrole is reported therein.

A. O. Abdelhamid et al., Journal Fur Praktische Chemi, 331, pages 31–36 (1989) report the synthesis of substituted phenacylacetonitrile compounds using concentrated hydrochloric acid in acetic acid. However, only 2-amino-3-cyano-5-arylfurans are prepared from the substituted phenacylacetonitrile compounds.

It is therefore an object of the present invention to provide a new and efficient process for preparing 2-halo-3-substituted-5-arylpyrrole compounds.

SUMMARY OF THE INVENTION

The present invention relates to an efficient process for the preparation of 2-halo-3-substituted-5-arylpyrrole compounds of formula I

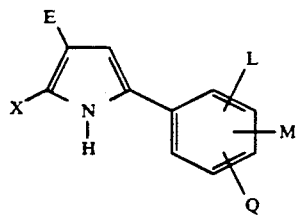

wherein
X is Cl or Br;
E is CN, $CO_2R$ or $CONRR^1$; R and $R^1$ are each independently hydrogen or $C_1$–$C_4$ alkyl;
L is hydrogen, F, Cl or Br;
M and Q are each independently hydrogen, F, Cl, Br, I, CN, $NO_2$, $CF_3$, $C_1$–$C_3$ alkyl, $C_1$–$C_3$ alkoxy, $C_1$–$C_3$ alkylsulfonyl, $C_1$–$C_3$ alkylsulfinyl, $C_1$–$C_3$ alkylthio or $R^2CF_2Z$;
Z is $S(O)_n$ or O;
n is an integer of 1 or 2; and
$R^2$ is hydrogen, F, $CHF_2$, $CHFCl$ or $CF_3$.

Surprisingly, it has been found that 2-halo-3-substituted-5-arylpyrrole compounds of formula I may be prepared by reacting a substituted acetonitrile compound of formula II

wherein E is as described above with a base and a substituted phenacyl halide compound of formula III

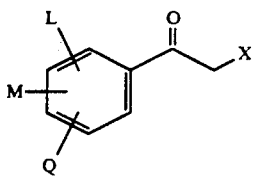

wherein X, L, M and Q are as described above in the presence of a solvent to obtain a substituted phenacylacetonitrile compound of formula IV

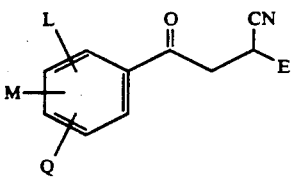

wherein E, L, M, and Q are as described above and reacting said formula IV compound in a solvent saturated with an excess of a hydrogen halide.

DETAILED DESCRIPTION OF THE INVENTION

One of the preferred embodiments of the present invention involves reacting a formula II substituted acetonitrile compound as described above with at least about 1 molar equivalent, preferably about 1 to 3 molar equivalents, of a base and at least about 1 molar equivalent, preferably about 1 to 3 molar equivalents, of a formula III substituted phenacyl halide compound as described above in the presence of a solvent preferably at a temperature range of about $-5°$ C. to 40° C. to form a formula IV substituted phenacylacetonitrile compound as described above and reacting the formula IV compound in a solvent saturated with an excess of a hydrogen halide preferably hydrogen chloride or hydrogen bromide at a temperature range of about 0° C. to 50° C. to form 2-halo-3-substituted-5-arylpyrrole compounds of formula I.

The formula I compounds may be isolated by conventional techniques such as dilution of the reaction mixture with water and filtration or, alternatively, extraction with a suitable solvent. Suitable extraction solvents include water-immiscible solvents such as ether, ethyl acetate, toluene, methylene chloride and the like.

Bases suitable for use in the process of the present invention include alkali metal $C_1$–$C_6$ alkoxides, alkali metal hydroxides, alkali metal hydrides, alkali metal carbonates, $C_1$–$C_4$ trialkylamines and pyridine. Preferred bases are potassium tert-butoxide, sodium methoxide and sodium hydride.

Reaction solvents suitable for use in the present invention include organic solvents such as ether, tetrahydrofuran, chlorinated hydrocarbons, $C_1$–$C_6$ alcohols and mixtures thereof. Chlorinated hydrocarbons and tetrahydrofuran are preferred reaction solvents.

Formula II substituted acetonitriles are prepared according to the procedures of A. R. Surrey, Journal of the American Chemical Society, 65, pages 2471–2472, 1943; F. B. Thole et al., Journal of the Chemical Society, 99, pages 422–448, 1911; P. Ruggli et al., Helvetica Chimica Acta, 25, pages 35–39, 1942; and E. P. Kohler et al., Organic Synthesis, 3, pages 53–56, 1923.

Certain starting formula III substituted phenacyl halides are prepared according to the procedures of J. P. Schaefer et al., Journal of Organic Chemistry, 28, page 1128, 1963; J. B. Rather et al., Journal of the American Chemical Society, 41, pages 75–83, 1919; W. D. Langley, Organic Syntheses Collective Volume I, ed. Henry Gilman (New York: John Wiley and Sons, 1958), pages 127–128; and M. A. Collet, Comptes rendus hebdomadaires des seances de l'Academie des Sciences, 125, pages 717–719, 1897.

Conversion of 2-halo-5-arylpyrrole-3-carbonitrile to the corresponding formula V, 2,4-dihalo-5-arylpyrrole-3-carbonitrile, is readily achieved by reaction of the above 2-halo-5-arylpyrrole-3-carbonitrile with at least about 1 equivalent of a sufuryl halide, bromine or chlorine, in the presence of a solvent such as dioxane, ether, tetrahydrofuran, acetic acid, a chlorinated hydrocarbon solvent or mixtures thereof. Other effective halogenating agents that may be employed in the above reaction include sodium hypochlorite, t-butylhypochlorite, N-bromosuccinimide and the like. The reaction may be illustrated as follows:

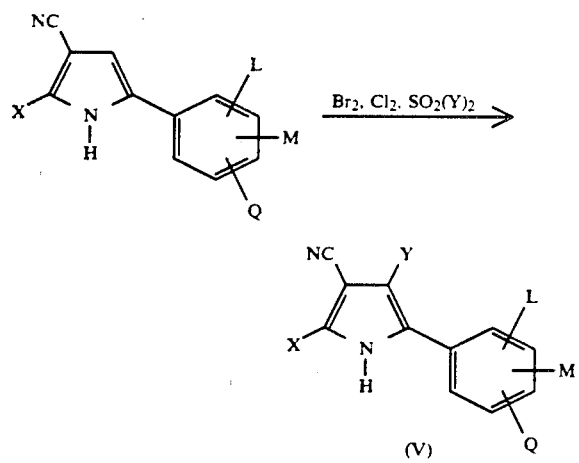

wherein
X is Cl or Br;
Y is Cl or Br;
L is hydrogen, F, Cl or Br;
M and Q are each independently hydrogen, F, Cl, Br, I, CN, $NO_2$, $CF_3$, $C_1$–$C_3$ alkyl, $C_1$–$C_3$ alkoxy, $C_1$–$C_3$ alkylsulfonyl, $C_1$–$C_3$ alkylsulfinyl, $C_1$–$C_3$ alkylthio or $R^2CF_2Z$;
Z is $S(O)_n$ or O;
n is an integer of 1 or 2; and
$R^2$ is hydrogen, F, $CHF_2$, CHFCl or $CF_3$.

N-substituted formula V 2,4-dihalo-5-arylpyrrole-3-carbonitrile compounds may be prepared by reacting the formula V pyrrole with an alkylating or an acylating agent in the presence of an alkali metal alkoxide or hydride. The reactions may be illustrated as follows:

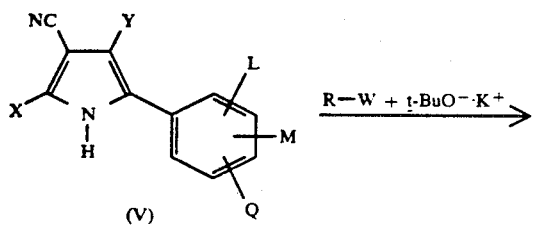

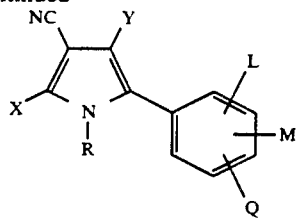

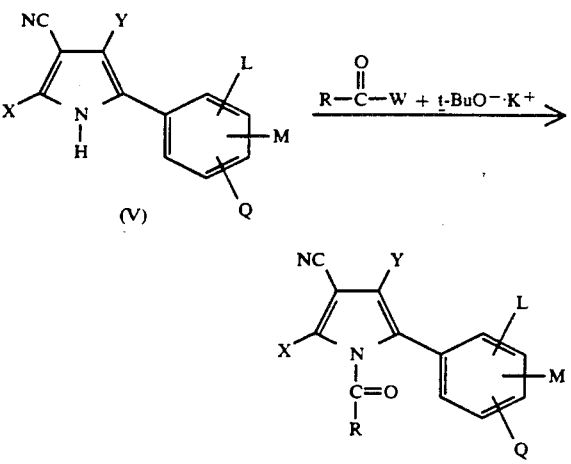

wherein
X, Y, L, M and Q are as described above for formula V and
W is Cl, Br or I; and
R is $C_1$–$C_6$ alkyl optionally substituted with one to three halogen atoms, one cyano, one $C_1$–$C_4$ alkoxy, one $C_1$–$C_6$ alkylcarbonyloxy group, one $C_1$–$C_6$ alkoxycarbonyl group or one benzyloxy group.

In those instances where the formula I pyrrole ring substituent E is $CONRR^1$ and R and $R^1$ are hydrogen, the amide may be converted by conventional means to the desired nitrile (E≡CN) using reagents such as phosphorus pentoxide or phosphorus oxychloride as described in *Advanced Organic Chemistry*, Jerry March, 3rd Edition, John Wiley and Sons, N.Y. 1985, P. 932. Likewise, in those instances where R is H and $R^1$ is $C_1$–$C_4$ alkyl, the same result may be achieved through the use of $PCl_5$ as described in *Advanced Organic Chemistry*, Jerry March, 3rd Edition, John Wiley and Sons, N.Y. 1985, P. 933.

Pyrrole amides suitable for conversion to the nitrile may be made directly from E—$CH_2$—CN where E is $CONRR^1$ or they may be prepared from the pyrrole resulting from the synthesis where E is $CO_2R$ and R is hydrogen or $C_1$–$C_4$ alkyl. In this case, the acid (R=H) may be converted to the amide by reaction with an amine, $RR^1NH$, in the presence of a coupling agent such as dicyclohexylcarbodiimide as described in *Advanced Organic Chemistry*, Jerry March, 3rd Edition, John Wiley and Sons, N.Y. 1985, P. 372. When R is $C_1$–$C_4$ alkyl, the conversion may be effected by direct reaction with an amine $RR^1NH$ or by first hydrolyzing the ester, $CO_2R$, to the acid, $CO_2H$, and proceeding as described above.

In order to facilitate a further understanding of the invention, the following examples are presented to illustrate more specific details thereof. The invention is not to be limited thereby except as defined in the claims.

EXAMPLE 1

Preparation of (3,4-Dichlorophenacyl)malononitrile

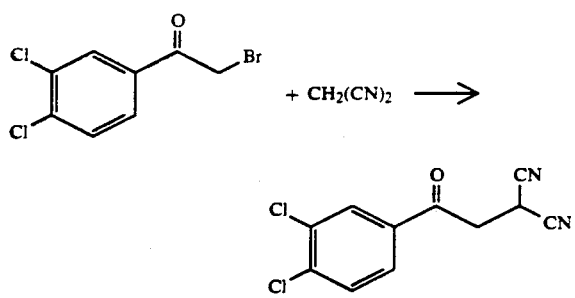

Malononitrile (9.9 g, 0.15 mol) is added to a 0° C. mixture of potassium tert-butoxide (18.5 g, 0.165-mol) and tetrahydrofuran (600 mL). After twenty minutes, 2,4-dichlorophenacyl bromide (41.0 g, 0.15 mol) is added dropwise to the reaction mixture and stirring is continued at 0° C. for 40 minutes. The solvent is removed in vacuo and the residue is diluted and triturated with water to give solids. The solids are collected and dried to give the title compound as a beige solid (37 g, 97.5%, mp 142°-145° C.). Identified by IR and NMR spectral analyses.

Following the procedure of Example 1, the following analogs are prepared

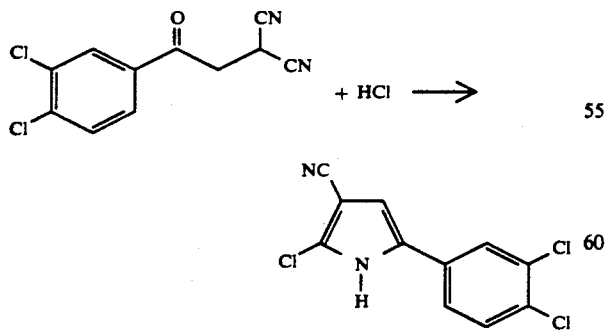

| L | M | Q | mp °C. |
|---|---|---|---|
| H | 4-Cl | H | 143-145 |
| H | 4-Br | H | 160-164 |
| H | 4-OCHF$_2$ | H | 125-129 |
| H | 4-Br | 3-Cl | — |
| H | 4-CF$_3$ | 3-F | — |
| 2-F | 4-CN | 3-Cl | — |

EXAMPLE 2

Preparation of 2-Chloro-5-(3,4-dichlorophenyl)pyrrole-3-carbonitrile

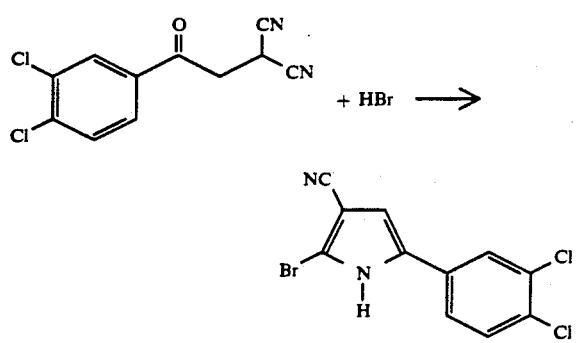

Hydrogen chloride gas is bubbled through a mixture of (3,4-dichlorophenacyl)malononitrile (8.3 g, 0.333 mol), ether (150 mL) and chloroform (100 mL) at a moderate rate, keeping the reaction mixture temperature below 35°-40° C. After 25 minutes, TLC shows the reaction is complete by UV analysis. The brown reaction mixture is poured into an ice-water mixture and extracted with ether. The combined organic extracts are washed with brine, dried over anhydrous magnesium sulfate and concentrated in vacuo to obtain a brown solid. The brown solid is washed with methylene chloride and filtered to give the title product as an off-white solid (6.7 g, 76%, mp >200° C.). Identified by IR and NMR spectral analyses.

EXAMPLE 3

Preparation of 2-Bromo-5-(3,4-dichlorophenyl)pyrrole-3-carbonitrile

Hydrogen bromide gas is bubbled through a mixture of (3,4-dichlorophenacyl)malononitrile (10.0 g, 0.0395 mol) in ether (150 mL) and chloroform (100 mL) at a moderate rate, keeping the reaction mixture temperature below 35°-40° C. After ten minutes, TLC shows the reaction is complete by UV analysis. The reaction mixture is poured into an ice-water mixture, the layers are separated and the aqueous layer is extracted with ether. The combined organic layer and ether extracts are dried and concentrated in vacuo to give a brown solid. The brown solid is washed with methylene chloride and filtered to obtain the title compound as an off-white solid (3.0 g, 24%, mp >200° C.) which is identified by IR and NMR spectral analyses.

Microanalysis: C$_{11}$H$_5$BrCl$_2$N$_2$: Calcd: C, 41.77%; H, 1.58%; N, 8.86%. Found: C, 42.46%; H, 1.75%; N, 8.72%.

Following the procedure of Examples 2 and 3 the following compounds are prepared.

| X | L | M | Q | mp °C. |
|---|---|---|---|---|
| Cl | H | 4-CL | H | >200 |
| Cl | H | 4-Br | H | 195-200 |
| Br | H | 4-Cl | H | >200 |
| Cl | H | 4-OCHF$_2$ | H | 145-153 |
| Br | H | 4-Br | 3-Cl | — |
| Cl | H | 4-CF$_3$ | 3-F | — |
| Br | 2-F | 4-CN | 3-Cl | — |

EXAMPLE 4

Preparation of
3-(p-Chlorobenzoyl)-2-cyanopropionamide

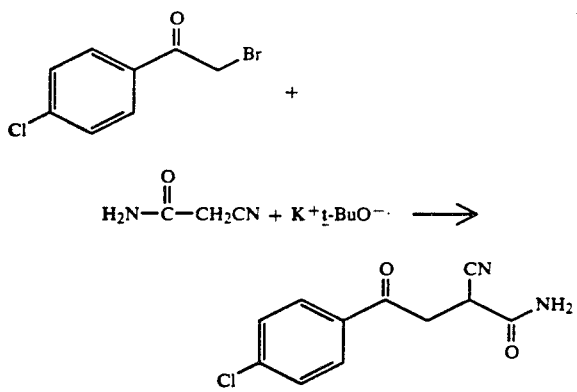

To a stirred mixture of cyanoacetamide (2.5 g, 0.030 mol) and tetrahydrofuran (160 mL) is slowly added potassium tert-butoxide (3.3 g, 0.030 mol) followed by p-chlorophenacyl bromide (7.0 g, 0.030 mol). The reaction is slightly exothermic and, after a short time, TLC shows none of the p-chlorophenacyl bromide present. The reaction mixture is diluted with water and brine and extracted with ether. The ether extract is dried and concentrated in vacuo to give a red oil. Upon addition of a hexane/ethyl acetate mixture (3:1) to the oil a solid forms and is collected by filtration to give the title product as a light yellow solid (1.4 g, 20%, mp 160°–161° C.) which is identified by IR and NMR spectral analyses.

EXAMPLE 5

Preparation of
2-Chloro-5-(p-chlorophenyl)pyrrole-3-carboxamide

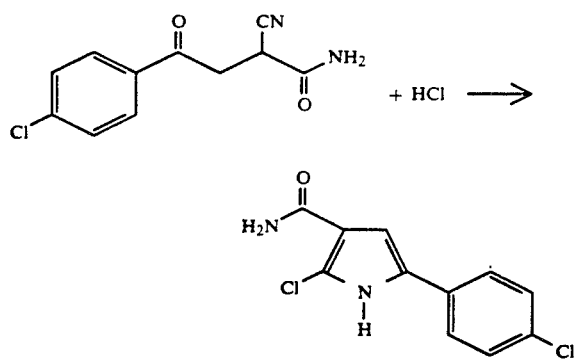

Into a mixture of 3-(p-chlorobenzoyl)-2-cyanopropionamide (1.0 g, 0.0042 mol), ether and chloroform is bubbled dry hydrogen chloride for about 10 minutes. TLC shows no remaining 3-(p-chlorobenzoyl)-2-cyanopropionamide. Solvent is removed in vacuo and the residue is distributed between ethyl acetate and water. The organic phase is separated, washed with water and brine and dried over magnesium sulfate. Solvent is removed and the resulting solid is triturated with ether and collected to give the title compound as a light brown solid (0.50 g, 46%, mp >200° C.). Identified by IR and NMR spectral analyses.

EXAMPLE 6

Preparation of Methyl
3-(p-chlorobenzoyl)-2-cyanopropionate

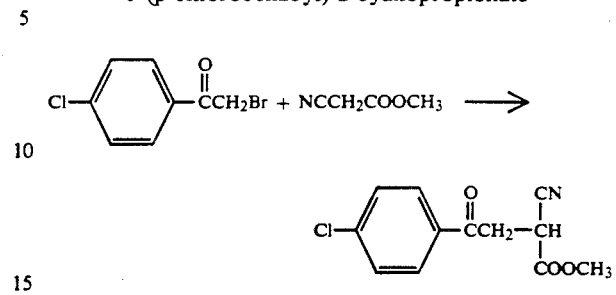

Diisopropylethyl amine (15.5 g, 0.12 mol) is added to dry tetrahydrofuran (60 mL) followed by a solution of methyl cyanoacetate (5.4 g, 0.055 mol) in tetrahydrofuran (10 mL). Finally, a solution of α-bromo-p-chloroacetophenone (11.0 g, 0.05 mol) in tetrahydrofuran (50 mL) is added. After three hours at room temperature, TLC (75/25 hexanes/ethyl acetate) indicates very little starting material. The reaction mixture is then heated at 50° C. for fifteen minutes, cooled and filtered. The filtrate is concentrated in vacuo to obtain an oil which solidifies when treated with dilute hydrochloric acid. The supernatant is decanted and the residue is taken up in ethyl acetate and dried. Work-up leaves a brown waxy solid (8.0 g, 64% crude yield) which on recrystallization from methanol gives the title compound as a white solid (4.3 g, mp 75°–79° C.).

Microanalysis: $C_{12}H_{10}ClNO_3$: Calcd: C, 57.27%; H, 4.00%; N, 5.56%. Found: C, 56.78%; H, 4.01%; N, 5.03%.

EXAMPLE 7

Preparation of methyl
2-chloro-5-(p-chlorophenyl)pyrrole-3-carboxylate

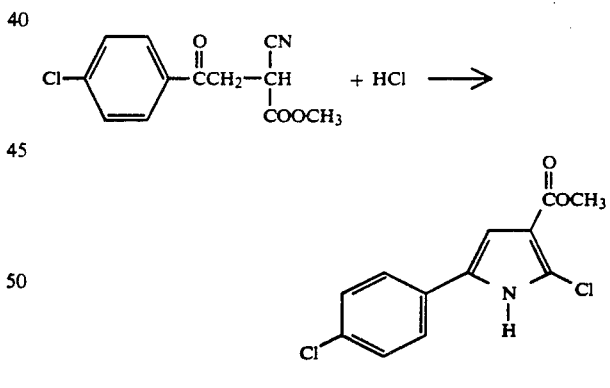

Methyl 3-(p-chlorobenzoyl)-2-cyanopropionate (4.6 g, 0.018 mol) is dissolved in 200 mL of a 1:1 mixture of ether and chloroform. Hydrogen chloride gas is then bubbled into the solution until TLC (3:1 hexanes/ethyl acetate) indicates the absence of starting material. During the introduction of gas, the temperature of the reaction mixture is kept below 30° C. with cooling. The reaction mixture is then filtered to remove an insoluble solid which is the title compound (1.2 g). The filtrate is washed several times with water. The organic layer is separated and dried over magnesium sulfate. Work-up leaves 3.2 g of a tacky solid which on boiling with 1,2-dichloroethane (30 mL) and filtering when cool gives an additional 1.2 g of the title compound. Total weight of the title compound obtained is 2.4 g (50%, mp 228°-232° C.).

Microanalysis: $C_{12}H_9NO_2Cl_2$: Calcd: C, 53.36%; H, 3.36%; N, 5.18%. Found: C, 53.23%; H, 3.41%; N, 5.35%.

EXAMPLE 8

Preparation of 2,4-Dichloro-5-(3,4-dichlorophenyl)pyrrole-3-carbonitrile

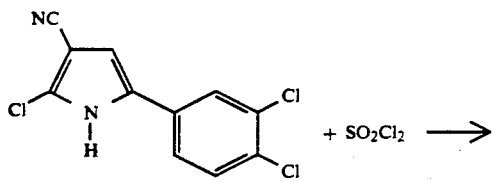

Sulfuryl chloride (1.8 g) is added dropwise to a 0° C. mixture of 2-chloro-5-(3,4-dichlorophenyl)pyrrole-3-carbonitrile, ether (30 mL) and acetic acid (30 mL). After stirring for 2 hours at 0° C., the reaction mixture is poured into an ice-water slurry. The cold mixture is diluted with hexane and the solids are collected and dried to give the title compound as a beige solid (mp >200° C.) which is identified by $^{13}C$ NMR spectral analysis.

Microanalysis: $C_{11}H_4Cl_4N_2$: Calcd: C, 43.14%; H, 1.31%; Cl, 46.41%; N, 9.15%. Found: C, 43.11%; H, 1.52%; Cl, 45.37%; N, 8.88%.

EXAMPLE 9

Preparation of 2,4-Dichloro-5-(3,4-dichlorophenyl)-1-(ethoxymethyl)-pyrrole-3-carbonitrile

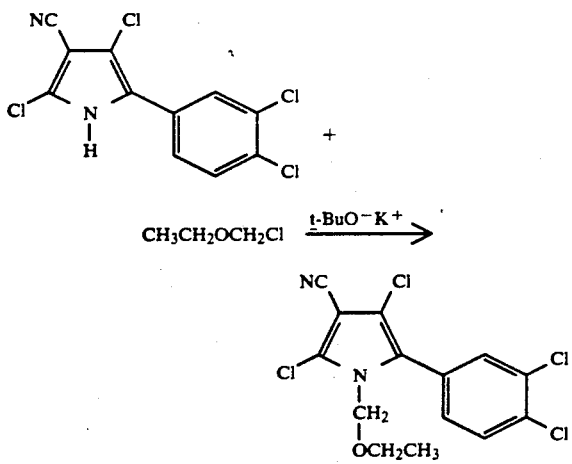

To a mixture of potassium tert-butoxide (0.62 g, 0.0055 mol) and tetrahydrofuran (50 mL) is added 2,4-dichloro-5-(3,4-dichlorophenyl)pyrrole-3-carbonitrile (1.3 g, 0.0043 mol) followed by chloromethyl ethyl ether (0.52 g, 0.0055 mol). After stirring the reaction mixture overnight, TLC (1:1 hexane/ethyl acetate) shows no remaining starting pyrrole and the reaction is concentrated in vacuo. Addition of water to the residue affords a solid which is collected and dried to give the title compound as a brown solid (1.4 g, 90%, mp 106°-109° C.) which is identified by IR and NMR spectral analyses.

Microanalysis: $C_{14}H_{10}Cl_4N_2O$: Calcd: C, 46.15%; H, 2.75%; N, 7.69%. Found: C, 46.74%; H, 2.72%; N, 7.42%.

I claim:

1. A process for the preparation of a 2-halo-3-substituted-5-arylpyrrole compound having the structural formula

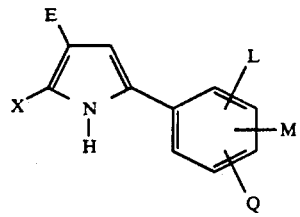

wherein

X is Cl or Br;

E is CN, $CO_2R$ or $CONRR^1$; R and $R^1$ are each independently hydrogen or $C_1$-$C_4$ alkyl;

L is hydrogen, F, Cl or Br;

M and Q are each independently hydrogen, F, Cl, Br, I, CN, $NO_2$, $CF_3$, $C_1$-$C_3$ alkyl, $C_1$-$C_3$ alkoxy, $C_1$-$C_3$ alkylsulfonyl, $C_1$-$C_3$ alkylsulfinyl, $C_1$-$C_3$ alkylthio or $R^2CF_2Z$;

Z is $S(O)_n$ or O;

n is an integer of 1 or 2; and $R^2$ is hydrogen, F, $CHF_2$, CHFCl or $CF_3$ which comprises reacting a substituted phenacylacetonitrile compound having the structural formula

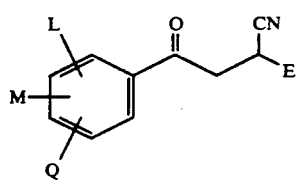

wherein E, L, M and Q are as described above in a solvent saturated with an excess of a hydrogen halide to form said 2-halo-3-substituted-5-arylpyrrole.

2. The process according to claim 1 wherein the hydrogen halide is hydrogen chloride or hydrogen bromide.

3. The process according to claim 1 wherein the solvent is selected from the group consisting of a chlorinated hydrocarbon, ether and a $C_1$-$C_6$ alcohol.

4. The process according to claim 1 wherein the temperature of the reaction mixture is about 0° C. to 50° C.

* * * * *